United States Patent [19]

Zopf et al.

[11] Patent Number: 5,753,630
[45] Date of Patent: *May 19, 1998

[54] METHOD FOR TREATING AND INHIBITING GASTRIC AND DUODENAL ULCERS

[75] Inventors: David A. Zopf, Strafford, Pa.; Paul M. Simon, Wilmington, Del.; Stephen Roth, Gladwyne; Edward J. McGuire, Furlong, both of Pa.; Dennis H. Langer, Princeton, N.J.

[73] Assignee: Neose Technologies, Inc., Horsham, Pa.

[ * ] Notice: The term of this patent shall not extend beyond the expiration date of Pat. No. 5,514,660.

[21] Appl. No.: 598,431

[22] Filed: Feb. 8, 1996

Related U.S. Application Data

[63] Continuation of Ser. No. 474,199, Jun. 7, 1995, Pat. No. 5,514,660, which is a continuation of Ser. No. 204,515, Mar. 2, 1994, abandoned, which is a continuation of Ser. No. 104,483, Jul. 28, 1993, abandoned, which is a continuation of Ser. No. 922,519, Jul. 31, 1992, abandoned.

[51] Int. Cl.$^6$ ............................ A61K 31/70; C07H 15/00
[52] U.S. Cl. .................... 514/25; 514/24; 514/42; 514/53; 514/54; 514/61; 536/4.1; 536/18.7; 536/22.1
[58] Field of Search ................... 514/24, 25, 42, 514/53, 54, 61; 536/4.1, 18.7, 22.1

[56] References Cited

U.S. PATENT DOCUMENTS

| | | | |
|---|---|---|---|
| 4,762,822 | 8/1988 | Ettinger | 514/25 |
| 4,923,980 | 5/1990 | Blomberg | 536/55.2 |
| 5,089,479 | 2/1992 | Krivan et al. | 514/25 |
| 5,164,374 | 11/1992 | Rademacher et al. | 514/23 |
| 5,211,937 | 5/1993 | Brandley et al. | 424/1.73 |
| 5,254,676 | 10/1993 | Sabesan et al. | 536/4.1 |
| 5,260,280 | 11/1993 | Isoda et al. | 514/25 |
| 5,300,302 | 4/1994 | Tachon et al. | 424/488 |
| 5,302,399 | 4/1994 | Otagiri et al. | 424/493 |
| 5,348,869 | 9/1994 | Stocker et al. | 435/125 |

OTHER PUBLICATIONS

Dunn et al. *Rev. Infectious Dis.* 1991, 12 Suppl. 8, S 657–664, no month available.

Lingwood et al. *Lancet* 1989, 2, 238–241, no month available.

Tzouvelekis et al. *Infection and Immunity* 1991, 59, 4252–4254, no month available.

Evans et al. *Infection an Immunity* 1989, 57, 2272–2278, no month available.

Evans et al. *Infection and Immunity* 1988, 56 2896–2906, no month available.

Smith et al., V. Ginsburg, ed. *Meth. Epiz.—Complex Carbohydrates C* 1978, 169–171, no month available.

Podolsky. *J. Biol. Chem.* 1985, 260 (14), 8262–8271, no month available.

Lambert *Rev. Infectious Dis.* 1991, 13 Supp. 8, S 691–695, no month available.

*Primary Examiner*—Kathleen K. Fonda
*Attorney, Agent, or Firm*—Oblon, Spivak, McClelland, Maier & Neustadt, P.C.

[57] ABSTRACT

A method for treating and/or inhibiting gastric and duodenal ulcers, comprising administering a pharmaceutical composition comprising an oligosaccharide of Formula I $$(\text{NeuAc-}\alpha(2\text{-}3)\text{-pGal-}\beta(1))\text{---}(\text{---X---})_m\text{---}(\text{---Y---})_n\text{---})_p\text{---Z}$$

wherein

X=a chemical bond or a group capable of linking the p galactose to either the linking group Y or the multivalent support Z;

wherein the $C_1$ glycosidic oxygen of galactose may be replaced by N, S or C;

Y=a linking group;

Z=a multivalent support;

m=0 or 1;

n=0 or 1; and p=an integer of 2–1,000 is described. Also described is a method for treating and/or inhibiting gastric and duodenal ulcers, comprising administering a pharmaceutical composition comprising an oligosaccharide of Formula II $$\text{NeuAc-}\alpha(2\text{ }3)\text{-pGal-}\beta(1)\text{-A}$$

wherein

A=a group capable of bonding to the p galactose;
wherein the $C_1$ glycosidic oxygen of galactose may be replaced by N, S or C.

9 Claims, No Drawings

METHOD FOR TREATING AND INHIBITING GASTRIC AND DUODENAL ULCERS

This application is a continuation of Ser. No. 08/474,199, filed Jun. 7, 1995, now U.S. Pat. No. 5,514,660, which is a continuation of Ser. No. 08/204,515, filed Mar. 2, 1994, now abandoned, which is a continuation of Ser. No. 08/104,483, filed Jul. 28, 1993, now abandoned, which is a continuation of Ser. No. 07/922,519, filed Jul. 31, 1992, now abandoned.

BACKGROUND OF THE INVENTION

1. Field of the Invention

The present invention relates a method for treating and inhibiting gastric and duodenal ulcers in a patient.

2. Discussion of the Background

Infection by the gram-negative, spiral, microaerophilic bacterium *Helicobacter pylori* (*H. pylori*), formerly known as *Campylobacter pylori* (*C. pylori*), is a primary cause of non-autoimmune gastritis, is a factor in peptic ulcer disease and is more common in patients with gastric carcinoma. First isolated by Warren (*Lancet* (1983) 1: 1273) and Marshall (*Lancet* (1983) 1: 1273–5), *H. pylori* has been isolated in gastric tissue biopsies in patients throughout the worlds. While the precise mechanism of inflammation is not well understood, *H. pylori* is found in association with the apical surfaces of gastric mucous-secreting cells.

Due to the site specificity of attachment, it has been suggested that there are specific attachment sites for *H. pylori* which exist on gastric and duodenal mucous-secreting cells. Numerous studies have been undertaken to attempt to identify the specific binding site of *H. pylori*.

Evans et al (*Infection and Immunity* (1988) 56: 2896–2906) reported that *H. pylori* binding to an erythrocyte receptor, as measured by hemagglutination inhibition, is preferentially inhibited by N-acetylneuraminyl-$\alpha(2\rightarrow3)$-Gal $\beta1\rightarrow4$ Glc (herein after NeuAc$(2\rightarrow3)$-lactose) as compared with N-acetylneuraminyl-$\alpha(2\rightarrow6)$-Gal $\beta1\rightarrow4$ Glc (herein after NeuAc$(2\rightarrow6)$-lactose). Sialoproteins which contain the NeuAc$(2\rightarrow3)$Gal isomer of NeuAc-lactose, i.e., human erythrocyte glycophorin A, fetuin, and human $\alpha_2$-macroglobulin, also inhibited *H. pylori* binding, but at higher concentrations (mg/ml) than that observed for NeuAc $(2\rightarrow3)$-lactose, while no inhibition was observed for the corresponding asialoglycoproteins.

Evans et al ibid, measured the hemagglutination inhibiting ability (HIA) of several compounds containing a NeuAc-lactose structure. Based on the hemagglutination inhibition activity, the researches determined that in order to produce 100% HAI, 1.000 mg/ml of $\alpha_2$-Macroglobulin was needed, 0.500 mg/ml of fetuin was needed, 0.250 mg/ml of Glycophorin A was needed and 0.078 mg/ml of bovine NeuAc-lactose was needed. Based on their hemagglutination inhibition studies the researches show fetuin to be about 2 times as effective as $\alpha_2$-Macroglobulin but only 0.156 times as effective as bovine NeuAc-lactose which comprises about 80% of NeuAc$(2\rightarrow3)$-lactose and 20% of NeuAc$(2\rightarrow6)$-lactose.

Evans et al (*Infection and Immunity* (1989) 57: 2272–2278) have also observed that *H. pylori* binds to monolayers of Y-1 mouse adrenal cells. But, this adherence can be prevented by pretreating the Y-1 cells with neuraminidase and is blocked by fetuin. However, it should be noted that there is no relationship between Y-1 mouse adrenal cells and gastric tissue.

Lingwood et al (*Lancet* (1989) 2: 238–241) have reported the isolation of a gastric glycerolipid material which they observed to behave as a receptor for *H. pylori*. The material was isolated from red blood cells, and mucosal scrapings of pig stomach and human stomach. The investigators postulated that the material was a sulphated alkylacylglycerolipid, but the actual structure of this material has not been reported. Subsequent investigations (Lingwood et al., *Infection and Immunity* (1992) 60: 2470–2474) showed that this receptor is phosphatidylethanolamine.

Lingwood et al., *Infection and Immunity* (1992) 61: 2472–2478 report that *Helicobacter pylori* specifically recognizes phosphatidylethanolamine, gangliotriaosylceramide and gangliotetraosylceramide and the isolation of an S-adhesin which is believed to be responsible for the lipid-binding specificity of this organism. However, none of the compounds which are reported as specifically recognized by *H. pylori*, are sialylated oligosaccharides.

Tzovelekis et al (*Infection and Immunity* (1991) 59: 4252–4253) reported binding inhibition of *H. pylori* to HEp-2 cells by gastric mucin. The investigators observed that purified mucin showed the greatest inhibition of *H. pylori* binding while asialomucin exhibits somewhat diminished inhibition and periodate-oxidized mucin exhibited the lowest level of binding. On these observations, the researchers concluded that sialic acids are at least partially responsible for the binding interaction between *H. pylori* and human gastric mucin. However, it should be noted that mucin contains a variety of different saccharide groups and linkages.

Boren et al (*Science* (1993) 262: 1892–1895) have reported that Lewis$^b$ blood group and H type I antigens mediate *H. pylori* attachment to human gastric mucosa.

Fauchere et al Microbial Pathogenesis, 1990 9 427–439 report that *H. pylori* adherence can be assessed by microtiter assays and involves a bacterial surface material which co-purifies with urease and is different from the N-acetylneuraminyl-lactose binding hemagglutinin.

Robinson et al report in *J. Med. Microbiol.* (1990) 33 277–284 that pre-treatment of human erythrocytes with neuraminidase from *Arthrobacter ureafaciens* and *Clostridium perfringens* abolished hemagglutination by the soluble, but not the cell-associated hemagglutinin, which suggests that sialic acid is not involved in binding inhibition of *H. pylori*.

Dunn et al Reviews of Infectious Diseases 1991; 13 (Suppl 8): (S657–64) report binding inhibition studies by Mean Fluorescence Intensity by treatment of materials with a neuraminidase. The researchers report a 16.8% decrease in MFI upon neuraminidase treatment of N-acetylneuraminyllactose of 16.8%, a 29.8% reduction with fetuin and an 8.6% reduction of asialofetuin. However, the researchers report a 30% increase upon treatment of KATO cells with neuraminidase. Such results call into question the role of sialylation in the site specific binding of *H. pylori*.

Saitoh et al report a sulfate-containing glycerolipid as a ligand which is specifically recognized by *H. pylori*.

While there have been numerous studies into compounds with *H. pylori* binding inhibition, it clear that the literature is replete with conflicting evidence.

Moreover, there is even a lack of a consensus as to the significance of the methods of testing for *H. pylori* binding inhibition. Hemagglutination assays have been used by many different researchers (see for example Evans et al (*Infection And Immunity* (1988) 56: 2896–2906), however Figueroa et al report in Journal of Infection (1992) 24 263–267, an adherence mechanism, which is not depending on the expression of specific hemagglutinin antigen. This report openly questions the relationship between hemagglutination inhibition and *H. pylori* binding inhibition. Furthermore, many of the cell surface adhesion systems, used to test for *H. pylori* binding inhibition, have no relationship to gastric tissue at all.

In addition to the numerous binding inhibition studies, methods have been pursued to treat gastric and duodenal ulcer patients.

Colloidal bismuth subcitrate (CBS) has been used successfully in treating both gastric and duodenal ulcer diseases (for a review, see Lambert in *Reviews of Infectious Diseases* (1991) 13 (Suppl. 8): S691–5. CBS has proven effective as a histamine $H_2$ antagonist and has been associated with lower relapse rates after cessation of therapy attributed to CBS's ability to eradicate *H. pylori*. Bismuth subsalicylate (BSS) has also been observed to inhibit *H. pylori*.

Coleman et al (U.S. Pat. No. 4,935,406) reported a method for relieving gastrointestinal disorder, resulting from *H. pylori* population, through the administration of bismuth (phosph/sulf)ated saccharide compositions. The saccharide compositions according to this method are simple phosphates and sulfates of aldose and ketose monosaccharides.

Clinical trials have been reported (Evans et al, *Ann. Internal Med.* (1991) August 15, 115(4): 266–9) in treating *H. pylori* using ranitidine in conjunction with a "triple therapy" of amoxicillin or tetracycline, metronidazole (an antiprotozoal), and BSS. The clinical studies suggested that ulcer healing was more rapid in patients receiving ranitidine plus the "triple therapy" than in patients receiving ranitidine alone.

The strong role that *H. pylori* plays in peptic ulcers has led to an announcement in February 1994 by an independent advisory panel of experts convened by the National Institutes of Health, to advise that patients diagnosed with peptic ulcers and *H. pylori* be treated for two weeks with a combination of antibiotics. A copy of the Consensus Development Conference Statement *Helicobacter pylori in Peptic Ulcer Disease* is available from the National Institutes of Health. There was no recommendation for any other type of therapy.

However, long-term eradication of this organism has been difficult with these therapies. The antibiotic approach runs the risk of the development of new antibiotic resistant strains. In addition, there are side affects associated from long term antibiotic therapy, which are unpleasant and make compliance with such a treatment regime more difficult. Thus, a method of treating *H. pylori* with good long-term eradication has not yet been developed.

As evidenced by the prior art identified above, there are a variety of structurally diverse compounds identified as candidates for being responsible for site specific attachment of *H. pylori*. The state of the art is further complicated by the variety of different in vitro assays used for predicting *H. pylori* binding inhibition, for which there is no identified correlation with effective *H. pylori* binding inhibition in mammals (Figueroa et al *Journal of Infection* (1992) 24 263–267). Even though 3' sialyl lactose has previously been identified as having hemagglutination inhibiting activity, and therefore speculatively identified as being a gastric colonization factor (Evans et al (*Infection and Immunity* (1988) 56: 2896–2906)) it was only one compound of many identified as possible candidates. The same publication, also reports the same activity, albeit only 0.156 times as great, for the compound fetuin. Accordingly, the state of the art, would not allow one to have selected 3' sialyl lactose from the many other and structurally diverse compounds, as a particularly effective means for inhibiting *H. pylori* binding inhibition in mammals.

Based on the inventors' studies, it has now been discovered that 3' sialyl lactose is a surprisingly effective inhibitor of *H. pylori* binding inhibition in mammals. And this finding has been validated by the inventors through in vivo mammalian test data.

In addition, contrary to earlier reports, the inventors of the present invention have discovered that fetuin has minimal activity in inhibiting binding of *H. pylori* cells, in vitro. The inventors have discovered that the binding inhibition activity associated with fetuin, appears to be attributable to a high molecular weight impurity which is a contaminate of commercially available fetuin. Based on their assay, the inventors of the present invention have discovered that 3' sialyl lactose has an ability to inhibit binding of *H. pylori* to a degree far in excess of what would have been expected in light of that previously reported for fetuin. From previous reports, one would expect that 0.156 times as much 3' sialyl lactose would be needed to achieve the same effectiveness, as achieved with fetuin. But since the inventors of the present invention have discovered that fetuin has minimal effectiveness in binding inhibition of *H. pylori* cells, their discovery that 3' sialyl lactose surprisingly strongly inhibits *H. pylori*, provides that 3' sialyl lactose can be used in an amount far below that which would have been predicted from the prior art. It is on the basis of this discovery that the present inventors have realized that 3' sialyl lactose is unexpectedly superior in inhibiting *H. pylori* in mammals.

SUMMARY OF THE INVENTION

Accordingly, one object of the present invention is to a method for treating and/or preventing gastric and/or duodenal ulcers.

Another object of the present invention is to provide a method for inhibiting *Helicobacter pylori* infection and/or reinfection to mammalian tissue, including eliminating *Helicobacter pylori* from the stomach and/or duodenum of a patient in need thereof.

Another object of the present invention is to provide a pharmaceutical composition for inhibiting *Helicobacter pylori* infection or reinfection of mammalian tissue, including eliminating *Helicobacter pylori* from the stomach and/or duodenum of a patient in need thereof and for treating and/or preventing gastric and/or duodenal ulcers.

All of the above objects of the present invention and other objects which are apparent from the description of the invention given herein below have been discovered by the inventors to be satisfied by administering a composition comprising an oligosaccharide of Formula I

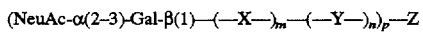

wherein

X=a chemical bond or a group capable of linking the p galactose to either the linking group Y or the multivalent support Z;

wherein the $C_1$ glycosidic oxygen of galactose may be replaced by N, S or C;

Y=a linking group;

Z=a multivalent support;

m=0 or 1;

n=0 or 1; and p=an integer of 2–1,000.

The present invention is also provided for by an oligosaccharide composition of Formula II NeuAc-α-(2–3)-Gal-β(1)-A wherein A=a group capable of bonding to the p galactose;
wherein the $C_1$ glycosidic oxygen of galactose may be replaced by N, S or C.

Contrary to previous reports (Evans et al (*Infection and Immunity* (1988) 56: 2896–2906)), the inventors of the present invention have discovered that an oligosaccharide of Formula I or Formula II, specifically NeuAc α(2→3)Gal β1–4 Glc (herein after also as 3' sialyl lactose) is dramatically more effective (more than 6.41 times more effective) at inhibiting *Helicobacter pylori* than is fetuin, when treating mammals. Specifically, Applicants have discovered that 3' sialyl lactose has unexpectedly improved activity in a method for treating *H. pylori* infections in mammals.

In addition, the inventors of the present invention have discovered that a multivalent presentation of an oligosaccharide (i.e. the oligosaccharide of Formula I) is unexpectedly superior, on a molar basis based on the oligosaccharide groups, than the monovalent presentation of the same oligosaccharide.

In addition, a method in which a pharmaceutical composition comprising the oligosaccharide of Formula I and/or Formula II alone, or in combination with an $R_2$ blocker, an antibiotic, oligosaccharide compounds and/or an antiulcerative compound is administered to a mammal, has been found by the inventors to be effective at inhibiting the binding of *Helicobacter pylori* to the gastric and duodenal mucosa and relieving the effects of gastric and duodenal ulcers.

DETAILED DESCRIPTION OF THE PREFERRED EMBODIMENTS

The following abbreviations are used throughout the text: "Gal" for galactose; "Glc" for glucose; "NeuAc" for N-Acetylneuraminic acid, "Gal" and "galactose", as they appear in Formula I and Formula II indicate the pyranose form of the sugar.

The oligosaccharide compound of Formula I

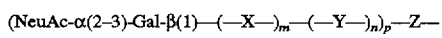

(NeuAc-α(2–3)-Gal-β(1)—(—X—)$_m$—(—Y—)$_n$)$_p$—Z— wherein

X=a chemical bond or a group capable of linking the p galactose to either the linking group Y or the multivalent support Z;

wherein the $C_1$ glycosidic oxygen of galactose may be replaced by N, S or C;

Y=a linking group;

Z=a multivalent support;

m=0 or 1;

n=0 or 1; and p=an integer of 2–1,000 is administered according to the present method.

For example X can be a substituted $C_{1-20}$ alkyl group, a substituted $C_{1-20}$ alkyl carboxylic ester group, a substituted $C_{1-20}$ alkyl carboxy amide group, a hydroxy terminated polyether, an amine terminated polyether, inositol, an aligosaccharide, a disaccharide or a monosaccharide with the terminal reducing end of the oligosaccharide, disaccharide or monosaccharide in the pyranose or open chain form, an azaoligosaccharide, an azadisaccharide or an azamonosaccharide with the terminal reducing end of the azaoligosaccharide, azadisaccharide or azamonosaccharide in the pyranose or open chain form, wherein said substitution is capable of reacting with the linking group of the multivalent support, such as a hydroxyl group or an amine group.

Preferably the group X is a monosaccharide hexose group such as glucose, N-acetylglucosamine, galactose, N-acetylgalactosamine, mannose, fucose, allose, altrose, gulose, idose, talose and rhamnose. In addition, a suitable group X is a reduced form of the above-identified hexose groups, such as glucitol.

When the group X is capable of bonding directly to the multivalent support, then n is 0.

When the $C_1$ glycosidic oxygen of galactose is capable of bonding directly to the multivalent support, then both m and n are 0.

A suitable linker group has one terminal portion of the Y group capable of bonding with the group X, while the other terminal end is capable of bonding with the multivalent support.

The chemistry necessary to link the group X and linking group Y and to link linking group Y to the multivalent support is well known in the field of linking chemistry. For example when X is a saccharide such as an oligosaccharide, a disaccharide or a monosaccharide, a bond between X and Y can be formed by reacting an aldehyde or carboxylic acid at $C_1$ of the X group or any aldehyde or carboxylic acid group introduced onto the X group by oxidation, with the Y group, to form a suitable bond such as —NH—, —N(R)— where R is $C_{1-20}$ alkyl, a hydroxyalkylamine, an amide, an ester, a thioester, a thioamide.

When X is a saccharide such as an oligosaccharide, a disaccharide or a monosaccharide, a bond between X and Y can be formed by reacting the $C_1$ hydroxyl group, in the pyranose form with an acylating agent and a molecular halide, followed by reaction with a nucleophile to form a suitable bond such as —NH—, —N(R)— where R is $C_{1-20}$ alkyl, —S— and —O—. This type of linking chemistry is described by Stowell et al Advances in Carbohydrate Chemistry and Biochemistry, 37 (1980) p 225+.

A suitable multivalent support is a compound with multiple binding sites to a terminal end of the linking group, which is not bound to the group X of the linking group, with multiple binding sites to the group X, or with multiple binding sites to the $C_1$ glycosidic oxygen of galactose. Examples include but are not limited to a polyol, a polysaccharide, polylysine, avidin, a polyacrylamide, dextran, lipids, lipid emulsions, liposomes, a dendritomer, human serum albumin, bovine serum albumin or a cyclodextrin.

The oligosaccharide is provided as a multivalent molecule according to Formula I. In this embodiment the oligosaccharide portion is bound to a multivalent support using known techniques so as to produce a conjugate in which more than one individual molecule of the oligosaccharide is covalently attached through a linker to the multivalent support. The multivalent support is sufficiently long to provide a multivalent molecule leaving from between 2–1, 000 (i.e. p=an integer of 2–1,000), preferably 2–100, more preferably 2–30 molecules of the oligosaccharide portion bound to the multivalent support.

The oligosaccharide portion can be bound to the multivalent support via the free anomeric carbon of the group X. Alternatively, the oligosaccharide portion can be bound via a phenethylamine-isothiocyanate derivative as described by Smith et al. Complex Carbohydrates part C, Methods in Enzymology, volume L, Ed by V. Ginsburg (1978), p 169–171. It is preferable that the oligosaccharide of Formula I remains soluble in water, however it is also possible to administer the oligosaccharide of Formula I in the form of polymer particles.

For example, the oligosaccharide portion of Formula I may be bound to a support to form a bead wherein the surface of the bead is bound with the oligosaccharide portion of Formula I.

The oligosaccharide composition of Formula II $$\text{NeuAc-}\alpha(2-3)\text{-Gal-}\beta(1)\text{-A}$$

wherein

A=a group capable of bonding to the p galactose;

wherein the $C_1$ glycosidic oxygen of galactose may be replaced by N, S or C;

is administered according to the present method.

For example A can be a $C_{1-20}$ alkyl group, a $C_{1-20}$ alkyl carboxylic ester group, a $C_{1-20}$ alkyl carboxy amide group, a polyether, inositol, an oligosaccharide, a disaccharide or a monosaccharide with the terminal reducing end of the oligosaccharide, disaccharide or monosaccharide in the pyranose or open chain form, an azaoligosaccharide, an azadisaccharide or an azamonosaccharide with the terminal reducing end of the azaoligosaccharide, azadisaccharide or azamonosaccharide in the pyranose or open chain form.

Preferably the group A is a monosaccharide hexose group such as glucose, N-acetylglucosamine, galactose, N-acetylgalactosamine, mannose, fucose, allose, altrose, gulose, idose, talose and rhamnose. In addition, a suitable group A is a reduced form of the above-identified hexose groups, such as glucitol.

The corresponding N and S glycosides of galactose can be prepared by conventional methods known to those of ordinary skill in the art from galactose followed by attachment of a sialyl acid group at the 3 position by conventional methods. The corresponding C glycoside of galactose can be made by conventional synthetic organic techniques, followed by attachment of a sialyl acid group at the 3 position by conventional methods.

Any known suitable pharmaceutically acceptable cations may be used with the oligosaccharides of Formula I and Formula II, to form a salt of the carboxylic acid group. Suitable cations, include conventional non-toxic salts including a metal salt such as an alkali metal salt (e.g. sodium salt, potassium salt, etc.) or an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N, N'-dibenzylethylenediamine salt, etc.), an organic acid salt (e.g. formate, acetate, trifluoroacetate, maleate, tartrate, methanesulfonate, benzenesulfonate, toluenesulfonate, etc.), an inorganic acid salt (e.g. hydrochloride, hydrobromide, sulfate, phosphate, etc.), a salt with an amino acid (e.g. arginine salt, aspartic acid salt, glutamic acid salt, etc.), and the like.

The oligosaccharides of the present invention may be obtained using any known method, including (1) enzymatically, using one of the inventor's method described in published international application WO 91/16449, (2) synthetically, using classical organic chemistry, (3) by degradation of a natural occurring oligosaccharide, glycolipid, or glycopeptide or (4) isolation from natural source such as bovine colostrum. The isolation of 3' sialyl lactose from bovine colostrum is described in Veh et al, Journal of Chromatography, 212, (1981) 313–322.

The oligosaccharides of Formula I and Formula II may be administered in conjunction with a known proton pump inhibitor or a known $H_2$ receptor antagonist. A representative proton pump inhibitor is omeprazole, and representative $H_2$ antagonists include cimetidine, ranitidine, nizatidine and famotidine. The amount of proton pump inhibitor and $H_2$ antagonist administered in conjunction with the present oligosaccharide is about the same amount administered for their known therapy. Accordingly, effective dosages of the proton pump inhibitor and $H_2$ can be determined by routine experimentation.

Alternatively a known antiulcerative compound may be used in conjunction with or as a replacement for the $H_2$ receptor antagonist. Suitable antiulceratives include aceglutamide aluminum complex, ε-acetamidocaproic acid zinc salt, acetoxolone, arbaprostil, benexate hydrochloride, bismuth subcitrate sol, bismuth subsalicylate, carbenoxolone, cetraxate, cimetidine, enprostil, esaprazole, famotidine, ftaxidide, gefarnate, guaiazulene, irsogladine, misoprostol, nazatidine, ornoprostil, γ-oryzanol, pifarnine, pirenzepine, plaunotol, ranitidine, rioprostil, rosaprostol, rotraxate, roxatidine acetate, sofalcone, spizofurone, sucralfate, teprenone, trimoprostil, trithiozine, troxipide, and zolimidine. The amount of antiulcerative administered in conjunction with the present oligosaccharide is about the same amount administered for its known therapy. Accordingly, effective dosage of the antiulcerative can be determined by routine experimentation.

Alternatively, the oligosaccharides of Formula I and Formula II may be administered in conjunction with an antibiotic with activity against *H. pylori*. Suitable antibiotics include metronidazole, tetracycline, bismuth, erythromycin, a macrolide, a quinolone, a cephalosporin and amoxicillin. The amount of antibiotic administered in conjunction with the present oligosaccharide is about the same amount administered for its known therapy. Accordingly, effective dosage of the antibiotic can be determined by routine experimentation.

Alternatively, the oligosaccharides of Formula I and Formula II may be administered in conjunction with a H-type 1 or Lewis$^b$ blood group antigen or an oligosaccharide such as NeuAc-α(2→6)-Gal β1→4 Glc. Suitable H-type 1 and Lewis$^b$ blood group antigens are reported in Boren et al. (*Science* (1993) 262: 1892–1895).

The anti-*H. pylori* compositions of the present invention contains the oligosaccharides of Formula I and Formula II in association with any suitable liquid or solid, pharmaceutically acceptable carrier or excipient, preferable in a form suitable for oral or enteral administration. In addition, the pharmaceutical compositions of the present invention are preferably pyrogen free.

The pharmaceutical compositions are usually administered as a mixture with a carrier suitably selected depending upon the route for administration using standard formulations. For example, the compound of the present invention may be administered in the form of tablets which may be prepared using known techniques by adding to a powder of the active ingredient of the present invention an excipient such as starch, lactose, sucrose, glucose, crystalline cellulose, calcium carbonate or kaolin, a hydroxypropylcellulose, a glucose solution, a sucrose solution, water or ethanol, a disintegrator such as starch, agar, gelatin powder, carboxymethylcellulose calcium (CMC-Ca), carboxymethylcellulose sodium (CMC-Na), crystalline cellulose, calcium carbonate or sodium hydrogencarbonate, or a lubricant such as magnesium stearate, calcium stearate, talc, macrogoal 4,000, macrogoal 6,000 or stearic acid.

The mixture is then subjected to compression molding by a conventional tableting method, and if necessary, applying a sugar coating by means of a concentrated sugar solution containing e.g. gum arabic, talc, polyvinylpyrrolidone, polyethyleneglycol and/or titanium oxide, applying a film coating by means of a film-forming agent composed of e.g. polyvinyl acetal diethylaminoacetate, hydroxypropylmethylcellulose, hydroxypropylcellulose, ethylcellulose or polyvinylpyrrolidone or applying an enteric coating by means of a film-forming agent composed of e.g. ethylcellulose phthalate, cellulose acetate phthalate or hydroxypropylmethylcellulose phthalate.

These pharmaceutical compositions may be in the form of granules or fine granules which may be prepared by adding to the active ingredient of the present invention a binder such as starch, gelatin, gum arabic, methylcellulose, sodium carboxymethylcellulose, heavy silicic anhydride or light silicic anhydride, followed by kneading and granulation by usual methods; or as a powder of the active ingredient of the present invention by itself; or as capsules which may be prepared by adding to the active ingredient of the present invention an excipient such as lactose, starch or crystalline cellulose and/or a lubricant such as magnesium stearate, calcium stearate or talc, and filling the mixture into capsules.

A solution or suspension may be prepared by adding any diluent customarily, used in the art. For example, suitable diluents include water, ethyl alcohol, propylene, glycol, polyoxyethylene sorbitol, and sorbitan esters. Sodium chloride, glucose or glycerol may be incorporated into such a liquid preparation in an amount sufficient to prepare an isotonic solution. The therapeutic composition may also further contain ordinary dissolving aids, buffers, pain-alleviating agents, art preservatives, and optionally coloring agents, fragrances, flavors, sweeteners and other pharmacologically active agents such are well known in the art.

Suitable compositions may take the form of a solution, suspension, tablet, coated tablet or any pharmaceutically acceptable form suitable for delivery to the stomach or duodenum.

According to a preferred embodiment of the present invention, the oligosaccharide or pharmaceutical compositions are administered orally or enterally to a patient in need thereof to inhibit H. pylori binding or eliminate H. pylori colonies from the patient's stomach and/or duodenum.

Typically, suitable patients are humans. However the present method is also applicable to treatment of animals, including but not limited to mammals such as pigs, cows, horses, sheep, goats, dogs, cats, rodents and non-human primates.

The method of the present invention is suitable for preventing and treating patients with duodenal ulcers, gastric ulcers and the prevention of gastric cancers in patients.

Suitable amounts of the pharmaceutical composition containing the oligosaccharides of Formula I and/or Formula II to be administered include those which produce an effective stomach concentration of oligosaccharide of from 1 µg to 10,000 mg/ml per dose, preferably 10 µg to 1,000 mg/ml, more preferably 0.5 mg to 50 mg/ml, most preferably 1 to 10 mg/ml. For example, based on an average human stomach volume of 500 ml, a dose of 3 gm would produce an effective stomach concentration of about 6 mg/ml.

Administration of the pharmaceutical composition comprising the oligosaccharide of Formula II is performed preferably to achieve a continuous effective stomach concentration of from 1 µg to 10,000 mg/ml per dose, preferably 10 µg to 1,000 mg/ml, more preferably 0.5 mg to 50 mg/ml, most preferably 1 to 10 mg/ml. This can be achieved by administration, at least daily, preferably twice daily, more preferably three times a day and most preferably four times a day.

When administered as a multivalent molecule a pharmaceutical composition comprising the oligosaccharide of Formula I is administered so as to achieve a continuous effective stomach concentration of from 1 µg to 1,000 mg/ml per dose, preferably 10 µg to 100 mg/ml, more preferably 50 µg to 5 mg/ml, most preferably 10 µg to 2 mg/ml. This can be achieved by administration, at least daily, preferably twice daily, more preferably three times a day and most preferably four times a day.

When a proton pump inhibitor, $H_2$ antagonist, or antiulcerative is coadministered, the composition is formulated to provide between 10–500 mg, preferably 100–300 mg of the proton pump inhibitor, $H_2$ antagonist, or antiulcerative daily. For example suitable therapies include administration of tetracycline (500 mg four times daily), bismuth subsalicylate (two tablets four times daily, with meals and at bedtime), and metronidazole (250 mg three times daily, with meals) each taken for a 14 day period. Dosage forms include such unit dosage forms such as tablets, capsules, solutions or suspensions.

After eradication of the H. pylori infection or treatment of the ulcer, maintenance dosages of are administered so as to achieve a continuous effective stomach concentration of from 1 µg to 1,000 mg/ml per dose, preferably 10 µg to 100 mg/ml, more preferably 50 µg to 5 mg/ml, most preferably 10 µg to 2 mg/ml. This can be achieved by administration, at least daily, preferably twice daily, more preferably three times a day and most preferably four times a day.

Other features of the invention will become apparent in the course of the following descriptions of exemplary embodiments which are given for illustration of the invention and are not intended to be limiting thereof.

EXAMPLE 1

Cell cultures, to test for the effectiveness of H. pylori binding inhibition were prepared from human carcinomas stomach cancer epithelial cells HuTu-80 obtained from the American Type Culture Collection Rockville, Md., according to a modified procedure from that reported in Fauchere et al Microbial Pathogenesis 1990; 9 427–439. The cultures were maintained in Basal medium Eagle containing 10% fetal calf serum in T-75 flasks, at 37° C. and a 5% $CO_2$ atmosphere. Cells were harvested by trypsin/EDTA release and plated on 96-well flat bottom microtiter plates. The microtiter plates were incubated for 2–3 days until the monolayers grew to confluence. Prior to binding inhibition tests, the monolayer was washed with Hanks Balanced Salt solution (HBSS) containing $Ca^{+2}$ and $Mg^{+2}$, 0.1% BSA, 50 mM HEPES, 0.01 phenol red or HBHPR.

H. pylori bacteria isolates were obtained from B. Marshall (from the University of Virginia) and grown on sheep blood agar, collected at 48 h, washed and suspended in a binding buffer of HBSS+0.1% bovine serum albumin+50 mM HEPES buffer+0.01% phenol red or HBHPR.

In order to test for H. pylori binding inhibition, the concentration of H. pylori which bound to the monolayer was assigned an intermediate $OD_{595}$ (optical density at 595 nm) (about 0.4 OD units). The same concentration of bacteria and test compound were combined for 10 minutes, then transferred onto the monolayer. Binding was allowed to occur for 20 min at room temperature under mild agitation. The unbound bacteria was washed away with 1 wash of HBHPR, then 2 washes of the same buffer without HEPES buffer (HBPR).

The amount of bacterial adhesion to the monolayer was measured by incubating with 50 µl urea-phenol red (UPR)

solution (0.2% urea, 0.03% phenol red in 0.85% NaCl). The presence of bound bacteria is indicated by the presence of bacterial urease which generates $NH_3$, which raises the pH and changes the color to purple, near at $OD_{595}$.

$IC_{50}$ in mg/ml was determined for each compound tested. The test data is reported below in Table 1:

TABLE 1

|  | Molar activity[2] | $IC_{50}$ mmol/ml |
|---|---|---|
| 3' sialyl lactose | 1 | $6 \times 10^{-3}$ |
| 6' sialyl lactose | — | $>1 \times 10^{-2}$ |
| 3' sialyl lactose-HSA[1] | $3.45 \times 10^{-3}$ | $2 \times 10^{-5}$ |
| lactose | — | $>1 \times 10^{-2}$ |
| HSA | — | $>1 \times 10^{-4}$ |

[1]3' sialyl lactose-HSA is a complex of 3' sialyl lactose with HSA, with about 20 molecules of 3' sialyl lactose bound to the HSA.
[2]relative to 3' sialyl lactose The data reveals that 3' sialyl lactose, when tested in a multivalent form was 290 times more effective on a molar basis than 3' sialyl lactose.

EXAMPLE 2

The binding inhibiting activity of fetuin was determined as follows:

Commercially available fetuin from Sigma Chemical was purified on a SEPHACRYL S-100 column (from Pharmacia) in aqueous 0.15M NaCl plus 0.05M Tris-HCl, pH 7.0 plus 0.02% $NaN_3$ and the $IC_{50}$ determined for each of the peaks isolated. $IC_{50}$s were determined using the HuTu-80 cell line monolayers. The results are shown below in Table 2, where fraction #3 corresponds with pure fetuin and fractions #1 and #2 correspond with unidentified high molecular weight impurities.

TABLE 2

| Fetuin fraction | $IC_{50}$ (mg/ml) | | |
|---|---|---|---|
|  | Expt A | Expt B | Expt C |
| #1 | 0.5 | 0.5 | 0.3 |
| #2 | 0.6 | 0.5 | 0.4 |
| #3 | * | * | 1.3 |
| crude fetuin | 1.33 | 1.4 | 1.5 |

*no means of inhibition observed even at the highest concentration tested of 2 mg/ml.

In vivo Animal test:

Gnotobiotic derived piglets (delivered by cesarean section and housed in a germ-free environment) were orally treated with 100 mg of 3' sialyl lactose in 5.0 ml of water.
Experiment A:

Six day old gnotobiotic piglets were orally treated with seven doses of 100 mg each of 3' sialyl lactose, at about 8 hour intervals. As a control, the piglets were administered water. The third administration of 3' sialyl lactose and control was accompanied with $2 \times 10^9$ live H. pylori. Two piglets were administered 3'sialyl lactose and 2 piglets were administered the control. The results are shown below in Table 3.
Experiment B:

Twenty one day old gnotobiotic piglets were orally treated with seven doses of 100 mg each of 3' sialyl lactose, at about 8 hour intervals. As a control, the piglets were administered water. The third administration of 3' sialyl lactose and control was accompanied with $4 \times 10^9$ live H. pylori. Four piglets were administered 3' sialyl lactose and 2 piglets were administered the control. The results are shown below in Table 3.

The piglets were evaluated by determining bacterial colonies in blood-agar as colony forming units/gram of gastric epithelium (CFU/g). Gastric epithelium homogenates were plated on agar in serial 1:10 dilutions and bacterial colonies were counted on the plates, with 20–200 colonies/plate after 5 days.

TABLE 3

|  | Experiment A | Experiment B | mean ± SD |
|---|---|---|---|
| 3' sialyl lactose | 5.44, 0 | 4.46, 25.5, 3.71, 2.48 | 6.9 ± 5.9 |
| control | 23.1, 28.8 | 24.1, 6.5 | 20.6 ± 8.3 |

EXAMPLE 3

An anti-Helicobacter composition is prepared by suspending 1 g of the 3' sialyl lactose in a mixture of water and propylene glycol.

EXAMPLE 4

An anti-Helicobacter composition is prepared by mixing 1 g of 3' sialyl lactose with 250 mg of the $H_2$ receptor antagonist ranitidine. The mixture is then suspended in a mixture of water and propylene glycol.

EXAMPLE 5

An anti-Helicobacter composition is prepared by mixing 1 g of 3' sialyl lactose with 250 mg of the proton pump inhibitor omeprazole. The mixture is then suspended in a mixture of water and propylene glycol.

EXAMPLE 6

An anti-Helicobacter composition is prepared by mixing 1 g of 3' sialyl lactose with 500 mg of a tetracycline. The mixture is then suspended in a mixture of water and propylene glycol.

EXAMPLE 7

As a therapeutic treatment, a patient infected with H. pylori is treated with the composition of Example 3. The patient is treated orally four times daily with each dosage providing an effective stomach concentration of 2 mg/ml. Therapy is continued for two weeks, after which examination showed eradication of the H. pylori bacteria. After eradication, maintenance therapy with the composition of the present invention is continued to prevent recurrence.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A pharmaceutical composition comprising, in association with a carrier or excipient suitable for oral or enteral administration, an oligosaccharide of Formula I

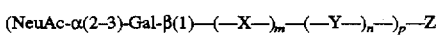

wherein

X=a group capable of linking the galactose to either the linking group Y or the multivalent support Z;

wherein the $C_1$ glycosidic oxygen of galactose may be replaced by N, S or C;

Y=a linking group;

Z=a multivalent support;

m=0 or 1;

n=0 or 1; and p=an integer of 2–1,000; and further comprising an element selected from the group consisting of an $H_2$ blocker an antiulcerative compound a proton pump inhibitor and a mixture thereof.

2. A pharmaceutical composition comprising, in association with a carrier or excipient suitable for oral or enteral administration, an oligosaccharide of Formula II $$NeuAc\text{-}\alpha\text{-}(2\text{-}3)\text{-}Gal\text{-}\beta(1)\text{-}A$$

wherein

A=a group capable of bonding to the galactose;

wherein the $C_1$ glycosidic oxygen of galactose may be replaced by N, S or C; and further comprising an element selected from the group consisting of an $H_2$ blocker, an antiulcerative compound, a proton pump inhibitor and a mixture thereof.

3. The pharmaceutical composition of claim 1, further comprising an element selected from the group consisting of an antibiotic, an oligosaccharide and a mixture thereof.

4. The pharmaceutical composition of claim 1, wherein X is selected from the group consisting of glucose, N-acetylglucosamine, galactose, N-acetylgalactosamine, mannose, fucose, allose, altrose, gulose, idose, talose, rhamnose and glucitol.

5. The pharmaceutical composition of claim 2, wherein A is selected from the group consisting of glucose, N-acetylglucosamine, galactose, N-acetylgalactosamine, mannose, fucose, allose, altrose, gulose, idose, talose, rhamnose and glucitol.

6. The pharmaceutical composition of claim 1, wherein Z is selected from the group consisting of a polyol, a polysaccharide, polylysine, avidin, a polyacrylamide, dextran, lipids, lipid emulsions, liposomes, a dendritomer, human serum albumin, bovine serum albumin or a cyclodextrin.

7. The pharmaceutical composition of claim 2, wherein said oligosaccharide of Formula II is NeuAc-$\alpha$(2–3)-Gal-$\beta$(1–4)Glc.

8. The pharmaceutical composition of claim 1, wherein X is 4-glucitol, m is 1, Y is phenethylamine-isothiocyanate, n is 1, p is 12–20 and Z is human serum albumin.

9. The pharmaceutical composition of claim 2 further comprising an element selected from the group consisting of an antibiotic, an oligosaccharide and a mixture thereof.

* * * * *